United States Patent
Masumoto (10) Patent No.: US 9,990,744 B2
(45) Date of Patent: Jun. 5, 2018

(54) IMAGE REGISTRATION DEVICE, IMAGE REGISTRATION METHOD, AND IMAGE REGISTRATION PROGRAM

(71) Applicant: FUJIFILM CORPORATION, Tokyo (JP)

(72) Inventor: Jun Masumoto, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 310 days.

(21) Appl. No.: 14/818,547

(22) Filed: Aug. 5, 2015

(65) Prior Publication Data

US 2016/0063707 A1 Mar. 3, 2016

(30) Foreign Application Priority Data

Aug. 27, 2014 (JP) .................................. 2014-172218

(51) Int. Cl.

| G06T 11/20 | (2006.01) |
|---|---|
| G06T 11/60 | (2006.01) |
| G06T 19/00 | (2011.01) |
| G06T 7/33 | (2017.01) |
| A61B 34/10 | (2016.01) |
| A61B 90/00 | (2016.01) |

(52) U.S. Cl.
CPC .............. *G06T 11/20* (2013.01); *A61B 34/10* (2016.02); *A61B 90/37* (2016.02); *G06T 7/337* (2017.01); *G06T 11/60* (2013.01); *G06T 19/00* (2013.01); *A61B 2034/107* (2016.02); *G06T 2207/10016* (2013.01); *G06T 2207/10068* (2013.01); *G06T 2207/10072* (2013.01); *G06T 2207/30244* (2013.01); *G06T 2210/41* (2013.01)

(58) Field of Classification Search
None
See application file for complete search history.

(56) References Cited

U.S. PATENT DOCUMENTS

| 2010/0225891 A1 | 9/2010 | Ota |
|---|---|---|
| 2015/0051617 A1 | 2/2015 | Takemura et al. |

FOREIGN PATENT DOCUMENTS

| JP | 2010-200894 A | 9/2010 |
|---|---|---|
| JP | 2010-205899 A | 9/2010 |
| JP | 2010-259497 A | 11/2010 |

(Continued)

OTHER PUBLICATIONS

J.P. Lewis, "Fast Template Matching", Vision Interface 95, Canadian Image Processing and Pattern Recognition Society, May 15-19, 1995, pp. 120-123.

(Continued)

*Primary Examiner* — Michelle Chin
(74) *Attorney, Agent, or Firm* — Sughrue Mion, PLLC (57) ABSTRACT

An initial registration unit performs initial registration between an intraoperative image and simulation information. A positional information obtaining unit obtains positional information indicating a relative positional difference between the intraoperative image after the initial registration and a newly obtained intraoperative image based on an unchanged position which is not changed during surgery included in the intraoperative images. A superimpose display unit registers the simulation information with the new intraoperative image based on the positional information and displays, on a display, the simulation information superimposed on the new intraoperative image.

13 Claims, 4 Drawing Sheets

(56) References Cited

FOREIGN PATENT DOCUMENTS

| JP | 2011-8397 A | 1/2011 |
| JP | 2013-34764 A | 2/2013 |
| JP | 2013-202313 A | 10/2013 |

OTHER PUBLICATIONS

J.P. Lewis, "Fast Normalized Cross-Correlation", Vision Interface, 1995, pp. 120-123, vol. 10, Issue 1.
David G. Lowe, "Distinctive Image Features from Scale-Invariant Keypoints", International Journal of Computer Vision (IJCV), 2004, pp. 91-110, vol. 60, No. 2.
Farhan Ullah, et al., "Orientation Code Matching for Robust Object Search", IEICE Transactions on Information and Systems, 2001, pp. 999-1006, vol. E84-D, No. 8.
Communication dated Nov. 15, 2016 from the Japanese Patent Office in counterpart application No. 2014-172218.
Communication dated May 16, 2017, from the Japanese Patent Office in counterpart Japanese application No. 2014-172218.
Communication dated Sep. 20, 2017 from the Japanese Patent Office in counterpart Application No. 2014-172218.

IMAGE REGISTRATION DEVICE, IMAGE REGISTRATION METHOD, AND IMAGE REGISTRATION PROGRAM

CROSS-REFERENCE TO RELATED APPLICATIONS

The present application claims priority under 35 U.S.C. § 119 to Japanese Patent Application No. 2014-172218, filed on Aug. 27, 2014. The above application is hereby expressly incorporated by reference, in its entirety, into the present application.

BACKGROUND OF THE INVENTION

Field of the Invention

The present invention relates to an image registration device, an image registration method, and an image registration program for registering simulation information relating to a surgery of a part to be operated on with an intraoperative image including the part to be operated on taken during the surgery and displaying the simulation information superimposed on the intraoperative image.

Description of the Related Art

Surgery simulations using three-dimensional medical images are popular in recent years. The surgery simulation uses visualization of a tissue or an organ to be operated on and structures around the tissue or organ from a medical image to simulate a procedure of an actual surgery. For example, in a simulation of segmental excision of the liver, tissues, such as the liver, the portal vein, veins, arteries, the body surface, bones, and a tumor, are extracted from tomographic images obtained by CT (Computed Tomography) or MRI (magnetic resonance imaging), and they are visualized as a three-dimensional image to generate a simulation image representing the operating field during surgery. Then, using the simulation image, the area to be excised to remove the tumor in the liver is calculated with a computer, and a surgery plan is developed to conduct the surgery.

On the other hand, there are demands to reference the simulation images during surgeries. To this end, some doctors bring simulation images printed on paper into their operating rooms, and some doctors display simulation images on a display device installed in their operating rooms. Then, the doctors conduct the surgery with looking at the actual part being operated of the patient and the simulation image printed on paper or displayed on the display device for confirmation.

It is, however, troublesome to conduct a surgery with alternately looking at the patient and the simulation image. To address this problem, techniques for imaging the part being operated on during a surgery to obtain an intraoperative image, and displaying the simulation image superimposed on the intraoperative image have been proposed. For example, Japanese Unexamined Patent Publication No. 2013-202313 (hereinafter, Patent Document 1) proposes a technique which involves: attaching an optical sensor or a magnetic sensor to a camera that images the part being operated on, to a surgical tool, or directly to the organ; calibrating the relative positional relationship between them; and registering the simulation image with the part being operated on by moving the simulation image to follow changes of the position and orientation of the camera after the calibration and movement of the organ to thereby display the simulation image superimposed on the image of the part being operated.

Further, a technique involving placing a marker on the part being operated on, detecting the marker position with a sensor to register the simulation image with the part being operated on, and displaying the resulting image on a head mount display (see Japanese Unexamined Patent Publication No. 2010-259497, hereinafter Patent Document 2), and a technique involving embedding markers in the part being operated on, detecting the markers with a sensor to register the simulation image with the part being operated on, and displaying the resulting image on a monitor (see Japanese Unexamined Patent Publication No. 2010-200894, hereinafter Patent Document 3) are proposed.

The techniques taught in Patent Documents 1 to 3, however, require use of an expensive sensor. Further, it is not easy to install a sensor in the operating room because of spatial limitations of the operating room. Still further, markers placed at the part being operated on can interfere with the surgery.

On the other hand, a technique for registering the simulation image with a patient image taken without using a sensor, or the like, has been proposed. For example, Japanese Unexamined Patent Publication No. 2010-205899 (hereinafter, Patent Document 4) proposes a technique which involves: generating an organ model from a three-dimensional image; obtaining an affine transformation function between each frame of an ultrasound image and the organ model to display the organ model superimposed on the ultrasound image real-time; and deforming the organ model based on the affine transformation function to superimpose the organ model on the ultrasound image. Further, although it does not pertain to medical images, a technique which involves displaying a template of eyebrows, for example, superimposed on a face image of the user while imaging the user's face real-time, and detecting change of the angle and enlargement or reduction of the user's face to move and enlarge or reduce the template to follow the movement of the user's face is proposed (see Japanese Unexamined Patent Publication No. 2011-008397, hereinafter Patent Document 5).

SUMMARY OF THE INVENTION

However, while the technique taught in Patent Document 4 does not use a sensor, the technique taught in Patent Document 4 obtains the affine transformation factor between each frame of the ultrasound image and the organ model to register the organ model with each frame. This requires deforming the organ model, and a large amount of computation is required to achieve the registration. On the other hand, the technique taught in Patent Document 5 superimposes the template of eyebrows on the user's face. The user's face may be oriented in various directions and enlarged or reduced to see whether the superimposed eyebrows look good on the face. In order to superimpose the template on the face image that changes on a moment-to-moment basis, it is necessary to perform the registration of each frame with respect to the entire part of the face, and a large amount of computation is required to achieve the registration. If the technique taught in Patent Document 4 or 5 is applied to registration between the simulation image and the intraoperative image, a large amount of computation is required, and it is difficult to quickly register the simulation image with the intraoperative image.

In view of the above-described circumstances, the present invention is directed to enabling quick registration of simulation information, such as a simulation image, with an intraoperative image including a part being operated on in a human body taken during surgery.

An aspect of the image registration device according to the invention is an image registration device comprising: an image obtaining unit for sequentially obtaining an intraoperative image including a part being operated on in a human body during a surgery; an information obtaining unit for obtaining simulation information relating to the surgery of the part being operated on; an initial registration unit that performs initial registration between the intraoperative image and the simulation information; a positional information obtaining unit for obtaining positional information indicating a relative positional difference between the intraoperative image after the initial registration and a newly obtained intraoperative image based on an unchanged position which is not changed during the surgery included in the intraoperative images; and a superimpose display unit for registering the simulation information with the new intraoperative image based on the positional information, and displaying on a display unit the simulation information superimposed on the new intraoperative image.

The "simulation information" as used herein refers to arbitrary information relating to the part being operated on. As the simulation information, for example, image information such as an image representing a three-dimensional shape of the part being operated on, an image representing three-dimensional shapes of the part being operated on and a structure included in the part being operated on, an image representing contours of the part being operated on and the structure, or a functional three-dimensional image obtained through a PET (Positron Emission Tomography) test or a NM (nuclear medicine) test may be used. Also, textual information such as names of the part being operated on and a structure included in the part being operated on, or lines indicating a position of excision on the part being operated on, and/or symbols such as arrows may be used as the simulation information.

The "unchanged position which is not changed during the surgery" as used herein refer to a position that is not changed in the course of the surgery, and examples thereof include a position where a surgical tool, such as forceps that holds the laparotomized portion, and a position of a part included in the intraoperative image other than the part being operated on. In a case where a portion of the part being operated on is excised, a portion of the part being operated on which will remain after the excision of the part being operated on may be used as the unchanged position during the surgery.

The image registration device according to the invention may further comprise an input unit for receiving specification of the unchanged position.

In the image registration device according to the invention, the simulation information obtaining unit may obtain a three-dimensional image about the part being operated on, and may generate the simulation information based on the three-dimensional image.

In the image registration device according to the invention, in a case where the part being operated on includes at least one structure, the simulation information may comprise an image representing three-dimensional shapes of the part being operated on and the at least one structure.

In this case, the image representing the three-dimensional shapes may include only contours of the part being operated on and the at least one structure.

Further, the image representing the three-dimensional shapes may have different transparency levels set for the part being operated on and the at least one structure.

Further, the image representing the three-dimensional shapes may have different colors set for the part being operated on and the at least one structure.

In the image registration device according to the invention, the simulation information may comprise an image representing a three-dimensional shape of the part being operated on.

In this case, the image representing the three-dimensional shape may include only a contour of the part being operated on.

In the image registration device according to the invention, the simulation information may comprise a functional three-dimensional image of the part being operated on.

In the image registration device according to the invention, the positional information obtaining unit may obtain, as the positional information, at least one of a translational component, a rotational component, and an enlargement factor between the intraoperative image after the initial registration and the newly obtained intraoperative image.

In the image registration device according to the invention, the information obtaining unit may obtain additional simulation information relating to a portion of the part being operated on, the portion being moved during the surgery, the initial registration unit may further perform initial registration between the intraoperative image and the additional simulation information, the positional information obtaining unit may further obtain, for the additional simulation information, additional positional information indicating a relative positional difference between the intraoperative image after the initial registration and the newly obtained intraoperative image based on a changeable position included in the portion that is moved during the surgery, and the superimpose display unit may register the additional simulation information with the new intraoperative image based on the additional positional information and may further display, on the display unit, the additional simulation information superimposed on the new intraoperative image.

An aspect of the image registration method according to the invention is an image registration method comprising the steps of: sequentially obtaining an intraoperative image including a part being operated on in a human body during a surgery; obtaining simulation information relating to the surgery of the part being operated on; performing initial registration between the intraoperative image and the simulation information; obtaining positional information indicating a relative positional difference between the intraoperative image after the initial registration and a newly obtained intraoperative image based on an unchanged position which is not changed during the surgery included in the intraoperative images; and registering the simulation information with the new intraoperative image based on the positional information, and displaying, on a display unit, the simulation information superimposed on the new intraoperative image.

It should be noted that the image registration method according to the invention may be provided in the form of a program for causing a computer to execute the image registration method.

According to the invention, an intraoperative image and simulation information are obtained, and initial registration between the intraoperative image and the simulation information is performed. Then, positional information indicating a relative positional difference between the intraoperative image after the initial registration and a newly obtained intraoperative image is obtained based on an unchanged position during surgery included in the intraoperative images. Based on the positional information, the simulation information is registered with the new intraoperative image, and the simulation information superimposed on the new intraoperative image is displayed on a display unit. As described above, in the invention, the positional information is obtained based on the unchanged position included in the intraoperative images, and therefore the information necessary for achieving the registration is obtained not from the entire intraoperative image. This allows obtaining the positional information with a smaller amount of computation, thereby allowing quick registration of the simulation information with the intraoperative image to display the superimposed image.

DESCRIPTION OF THE PREFERRED EMBODIMENTS

Figure 1:
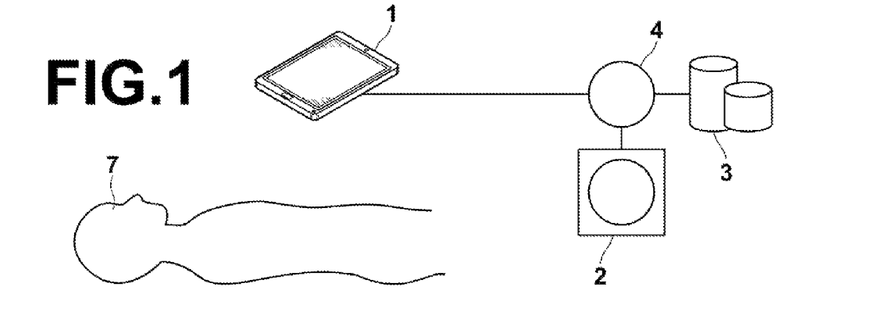
FIG. 1 is a diagram showing the hardware configuration of a surgery assistance system to which an image registration device according to an embodiment of the invention is applied.

Hereinafter, an embodiment of the present invention will be described with reference to the drawings. FIG. 1 is a hardware configuration diagram showing the outline of a surgery assistance system to which an image registration device according to the embodiment of the invention is applied. As shown in FIG. 1, in this system, an image registration device 1 according to this embodiment, a three-dimensional imaging apparatus 2, and an image storage server 3 are connected to each other to allow communication therebetween via a network 4.

The three-dimensional imaging apparatus 2 images a part to be operated on of a subject 7 to generate a three-dimensional image V0 showing the part, and is specifically a CT apparatus, an MRI apparatus, or a PET (Positron Emission Tomography) apparatus, for example. The three-dimensional image V0 generated by the three-dimensional imaging apparatus 2 is sent to and stored in the image storage server 3. It should be noted that, in this embodiment, the part to be operated on of the subject 7 is the liver, the three-dimensional imaging apparatus 2 is a CT apparatus, and the three-dimensional image V0 of the abdomen is generated.

The image storage server 3 is a computer that stores and manages various data, and includes a large-capacity external storage device and database management software. The image storage server 3 communicates with other devices via the wired or wireless network 4 to send and receive image data, etc. Specifically, the image storage server 3 obtains image data, such as the three-dimensional image V0 generated by the three-dimensional imaging apparatus 2, via the network, and stores and manages the image data in a recording medium, such as the large-capacity external storage device. The format of the stored image data and the communication between the devices via the network 4 are based on a protocol such as DICOM (Digital Imaging and Communication in Medicine).

The image registration device 1 is implemented by installing an image registration program of the invention on one computer. In this embodiment, the computer is a tablet-type terminal that is directly operated by a doctor who conducts diagnosis and is wireless connected to the network 4. The image registration program is distributed with being recorded in a recording medium, such as a DVD or CD-ROM, and is installed on the tablet-type terminal from the recording medium. Alternatively, the image registration program is stored in a storage unit of a sever computer connected to the network or a network storage in a state where it is externally accessible, and is downloaded and installed on the tablet-type terminal on demand.

Figure 2:
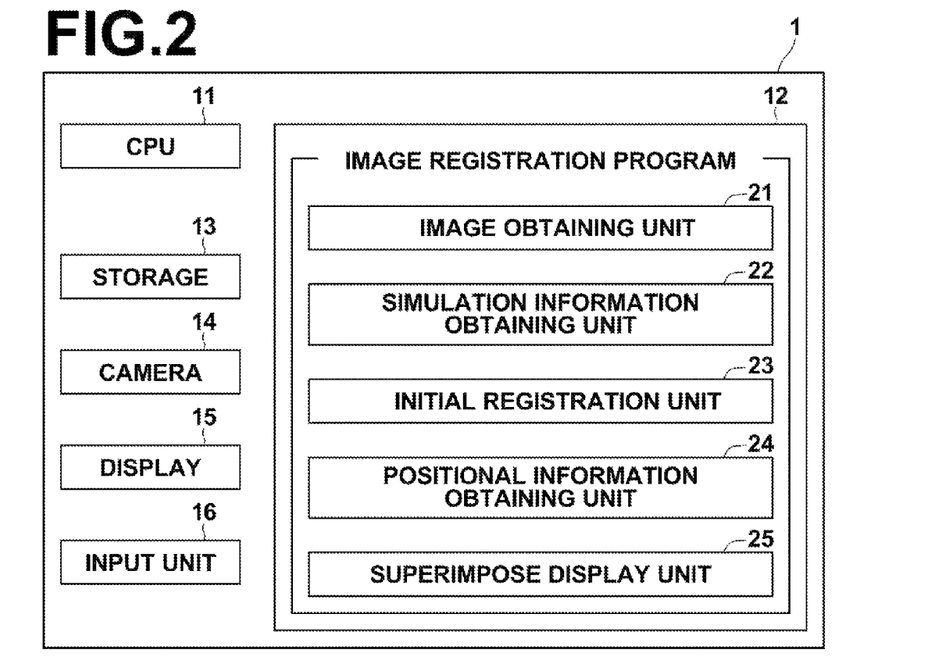
FIG. 2 is a diagram showing the schematic configuration of the image registration device that is implemented by installing an image registration program on a tablet-type terminal.

FIG. 2 is a diagram showing the schematic configuration of the image registration device which is implemented by installing the image registration program on the tablet-type terminal. As shown in FIG. 2, the image registration device 1 includes, as the standard configuration of the tablet-type terminal, a CPU 11, a memory 12, a storage 13, a camera 14, a display 15 such as a liquid crystal display, and an input unit 16 in the form of a touch panel.

The storage 13 stores various information including the three-dimensional image V0 obtained from the image storage server 3 via the network 4, and an image generated through processing by the image registration device 1.

The camera 14 includes a lens, an image sensor such as a CCD (Charge Coupled Device), an image processing unit for processing the obtained image to improve image quality, etc. The doctor images the liver of a laparotomized subject 7 during a surgery using the image registration device 1, i.e., the camera 14 of the tablet-type terminal, to obtain an intraoperative image T0 including the liver, which is the part being operated on of the subject 7. The intraoperative image T0 is a moving image with a given frame rate.

The memory 12 stores the image registration program. The image registration program defines, as operations to be executed by the CPU 11: an image obtaining operation of obtaining the three-dimensional image V0 taken with the three-dimensional imaging apparatus 2 and the intraoperative image T0 taken with the camera 14; a simulation information obtaining operation of obtaining simulation information relating to the surgery of the part being operated on; an initial registration operation of performing initial registration between the intraoperative image T0 and the simulation information; a positional information obtaining operation of obtaining positional information indicating a relative positional difference between the intraoperative image after the initial registration and a newly obtained intraoperative image based on an unchanged position which is not changed during surgery included in the intraoperative images; and a superimpose display operation of registering the simulation information with the new intraoperative image based on the positional information and displaying, on the display 15, the simulation information superimposed on the new intraoperative image.

When the CPU 11 executes the above-described operations according to the program, the tablet-type terminal functions as an image obtaining unit 21, a simulation information obtaining unit 22, an initial registration unit 23, a positional information obtaining unit 24, and a superimpose display unit 25. It should be noted that the image registration device 1 may include CPUs that execute the image obtaining operation, the initial registration operation, the positional information obtaining operation, and the superimpose display operation, respectively.

The image obtaining unit 21 obtains the three-dimensional image V0, and the intraoperative image T0 including the part being operated on of the subject taken with the camera 14 during surgery. If the three-dimensional image V0 has already been stored in the storage 13, the image obtaining unit 21 may obtain the three-dimensional image V0 from the storage 13. It should be noted that the intraoperative image T0 is taken by the doctor by imaging the liver of the laparotomized subject 7 from above.

The simulation information obtaining unit 22 generates the simulation information of the liver, which is the part to be operated on. To this end, the simulation information obtaining unit 22 first extracts the liver, which is the part to be operated on, and the hepatic artery, the hepatic vein, and a lesion included in the liver from the three-dimensional image V0. The simulation information obtaining unit 22 includes classifiers that determine whether or not each pixel of the three-dimensional image V0 is a pixel showing the liver, or the artery, the vein, or a lesion included in the liver (hereinafter, "the liver, etc.") The classifiers are obtained through machine learning using sample images of the liver, etc., according to a technique such as the Ada boosting algorithm. The simulation information obtaining unit 22 extracts the liver, etc., from the three-dimensional image V0 using the classifiers.

Then, the simulation information obtaining unit 22 generates an image showing the three-dimensional shapes of the liver, etc., as the simulation information S0. Specifically, a projection image of the extracted liver, etc., projected on a predetermined projection plane is generated as the simulation information S0. The projection plane may, for example, be a plane in front of the liver of the subject 7. A specific example of a projection method used is a known volume rendering technique.

Figure 3:
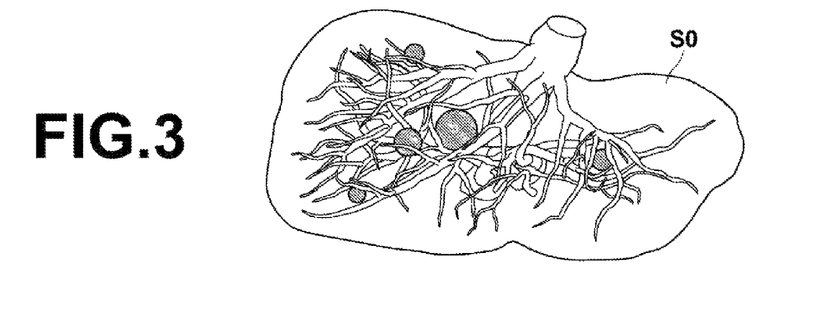
FIG. 3 is a diagram showing simulation information.

At this time, the simulation information S0 may be generated with different colors defined for the liver, and the hepatic artery, the hepatic vein, and the lesion included in the liver, or may be generated with different transparency levels defined for the liver, and the hepatic artery, the hepatic vein, and the lesion included in the liver. For example, the hepatic artery may be shown in red, the hepatic vein may be shown in blue, and the lesion may be shown in green, or the liver may be shown with an opacity level of 0.1, the hepatic artery and the hepatic vein may be shown with an opacity level of 0.5, and the lesion may be shown with an opacity level of 0.8. In this manner, the simulation information S0 as shown in FIG. 3 is generated. As described above, defining different colors or different opacity levels for the liver, and the hepatic artery, the hepatic vein, and the lesion included in the liver in the simulation information S0 facilitates distinguishing among the liver, and the hepatic artery, the hepatic vein, and the lesion included in the liver. It should be noted that both the different colors and the different transparency levels may be defined to generate the simulation information S0. The thus generated simulation information S0 is stored in the storage 13.

The simulation information S0 may include only the contours of the liver, etc. In this case, the operating field can still be easily seen on the display 15 when the simulation information S0 superimposed on the intraoperative image T0 is displayed, as described later.

Now, a process performed in this embodiment is described together with description of the initial registration unit 23, the positional information obtaining unit 24, and the superimpose display unit 25.

Figure 4:
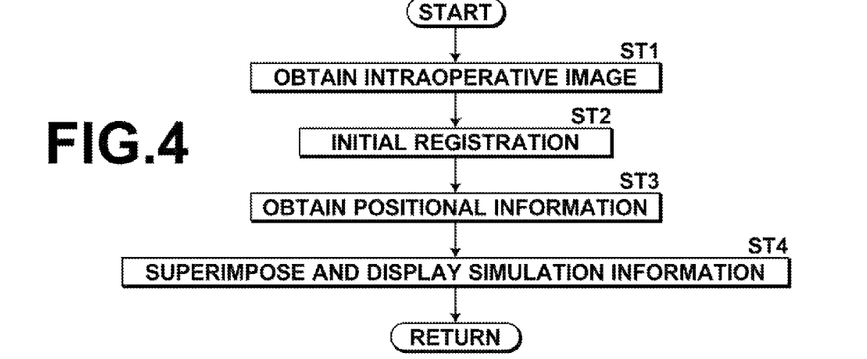
FIG. 4 is a flow chart showing a process performed in the embodiment.

FIG. 4 is a flow chart showing the process performed in this embodiment. It is assumed here that the simulation information S0 has already been generated and stored in the storage 13. First, the part being operated on of the subject 7 is imaged and the intraoperative image T0 is obtained (step ST1). It should be noted that the intraoperative image T0 is sequentially obtained at a given frame rate. Then, the initial registration unit 23 performs initial registration between the intraoperative image T0 and the simulation information S0 (step ST2).

Figure 5:
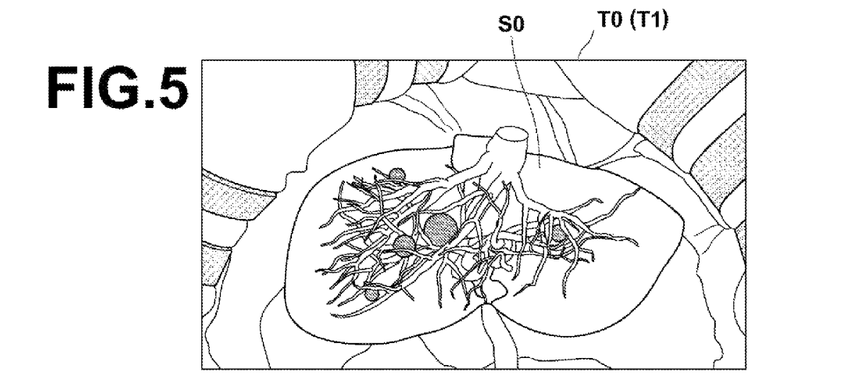
FIG. 5 is a diagram showing an image that is displayed on a display at the time of initial registration.

FIG. 5 is a diagram showing an image that is displayed on the display at the initial registration. At the initial registration, the initial registration unit 23 displays, on the display 15, the simulation information S0 superimposed on the intraoperative image T0. At this stage, the simulation information S0 is displayed at a predetermined position on the display 15. The displayed simulation information S0 can be translated, rotated, and enlarged or reduced by user's operation via the input unit 16, i.e., touch operation by the user on the display 15. It should be noted that, assuming that the x-axis and the y-axis are set along the plane in which the image is present, and the z-axis is set in the direction perpendicular to the image, the simulation information S0 can be rotated in any of the directions of the three axes. When the simulation information S0 is rotated in a plane other than the x-y plane, i.e., the simulation information S0 is rotated about the x-axis and/or the y-axis, the projection plane of the simulation information S0 is changed. When the projection plane is changed, the simulation information obtaining unit 22 generates the simulation information S0 again.

The intraoperative image T0 displayed at the initial registration may be a moving image or a still image, and it is a moving image in this embodiment. It is preferred that, at the initial registration, the position of the tablet-type terminal be adjusted such that the entire operating field is contained in the intraoperative image.

The doctor viewing the intraoperative image T0 and the simulation information S0 displayed on the display 15 translates, rotates, and enlarges or reduces the simulation information S0 such that the position of the simulation information S0 is registered with the position of the liver included in the intraoperative image T0. When the position of the simulation information S0 is registered with the position of the liver included in the intraoperative image T0, the doctor makes an instruction to end the initial registration via the input unit 16, and the initial registration is finished. It should be noted that the instruction to end the initial registration may be made by a predetermined operation on the input unit 16, such as touching a button for instructing to end the initial registration displayed on the display 15, double tapping, or the like. With this, the intraoperative image T0 which is displayed on the display 15 at the end of the initial registration is stored in the storage 13 as an initial intraoperative image T1.

It should be noted that, in this embodiment, the part being operated on is the liver, and it is possible that the liver will be excised and moved during surgery. To address such a situation, specification of an unchanged position, which is not moved during the surgery, on the intraoperative image T0 displayed on the display 15 is received during the initial registration in this embodiment. For example, on the intraoperative image T0 shown in FIG. 6, a position where a surgical tool, such as forceps 30, is present is not moved during surgery. Further, in a case where the left lobe of the liver is excised, the right lobe of the liver is not moved during surgery. In this embodiment, specification of an unchanged position which is not moved during surgery, such as a position O1 on the edge of the forceps 30 or a position O2 of the right lobe of the liver, is received via the input unit 16 and the unchanged position is stored in the storage 13.

Figure 7:
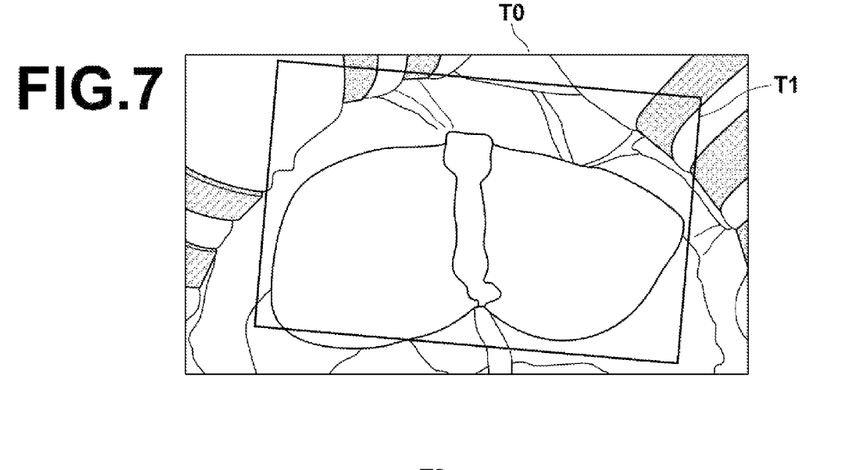
FIG. 7 is a diagram for explaining positional shift of a currently displayed intraoperative image from an initial intraoperative image.

After the initial registration, the doctor proceeds the surgery. During the surgery, the doctor cannot hold the tablet-type terminal above the subject 7, and imaging of the part being operated on with the tablet-type terminal is temporarily stopped. Thereafter, the part being operated on is imaged with the tablet-type terminal as necessary to confirm the position of the lesion, etc. At this time, the part being operated on is imaged with the tablet-type terminal at a position different from the position of the tablet-type terminal at the time of the initial registration. In such a situation, since the position of the camera 14 is different from the position of the camera when the initial intraoperative image T1 is obtained, the position of the intraoperative image T0 displayed on the display 15 differs from the position of the initial intraoperative image T1, as shown in FIG. 7. Then, based on the unchanged position which is not changed during surgery included in the intraoperative image T0, the positional information obtaining unit 24 obtains positional information indicating a relative positional difference between the initial intraoperative image T1 and the newly obtained intraoperative image T0 (step ST3).

Figure 6:
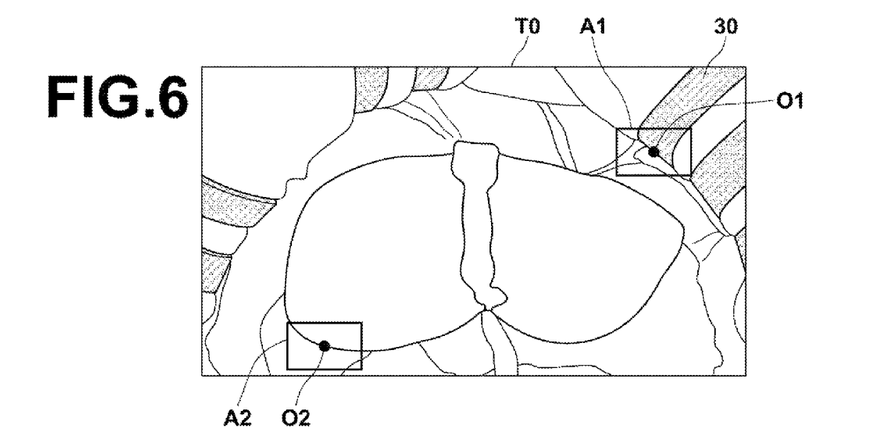
FIG. 6 is a diagram for explaining how a region with an unchanged position being the center thereof is set.

First, in order to obtain the positional information P0, the positional information obtaining unit 24 performs template matching of the intraoperative image T0 and the initial intraoperative image T1 with reference to the unchanged position. To achieve the template matching, a technique involving setting regions A1 and A2 with the unchanged positions O1 and O2 being the center of the regions on the initial intraoperative image T1, as shown in FIG. 6, and calculating at least one of a translational component, a rotational component, and an enlargement factor of the intraoperative image T0 relative to the initial intraoperative image T1 as positional information P0 based on the correspondence relationship among the regions A1 and A2 and the intraoperative image T0. It should be noted that the rotation herein refers to a two-dimensional rotation about the z-axis (i.e., a rotation in the x-y plane).

The positional information P0 indicates a relative positional difference of the currently displayed intraoperative image T0 relative to the initial intraoperative image T1. Therefore the positional information P0 is equivalent to a relative positional difference between the current position of the camera 14 and the position of the camera 14 at the initial registration.

The technique used to achieve the template matching is not limited to the above-described technique, and any other technique can be used, such as a fast template matching technique which performs matching for positions in the intraoperative image T0 that are similar to the initial intraoperative image T1 (J. P. Lewis, "Fast Template Matching", Vision Interface, Canadian Image Processing and Pattern Recognition Society, pp. 120-123, 1995 (see also the expanded and corrected version "Fast Normalized Cross-Correlation")), a technique using unchanged feature quantities with respect to rotational components to perform matching (D. G. Lowe, "Distinctive Image Features from Scale-Invariant Keypoints", International Journal of Computer Vision (IJCV), Vol. 60, No. 2, pp. 91-110, 2004), and a technique which involves encoding using given image information to increase robustness of template matching (F. Ullah et al., "Orientation Code Matching for Robust Object Search", IEICE Transactions on Information and Systems, Vol. E84-D, No. 8, pp. 999-1006, 2001).

Figure 8:
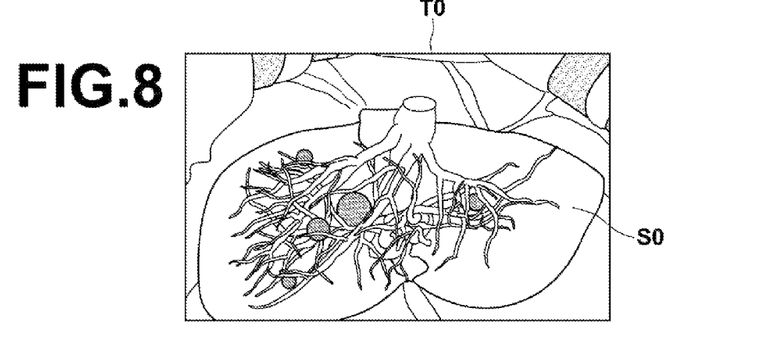
FIG. 8 is a diagram for explaining how the simulation information superimposed on the intraoperative image is displayed.

Based on the thus obtained positional information P0, the superimpose display unit 25 registers the simulation information S0 with the current intraoperative image T0 and displays the simulation information S0 superimposed on the current intraoperative image T0 (step ST4), and the process returns to step ST3. At this time, the simulation information S0 is translated, rotated, and/or enlarged or reduced based on the positional information P0. In this manner, the simulation information S0 is superimposed and displayed on the intraoperative image T0 such that the simulation information S0 is in the position corresponding to the position thereof registered with the initial intraoperative image T1, as shown in FIG. 8.

As described above, according to this embodiment, the positional information P0 indicating a relative positional difference between the intraoperative image T0 and the initial intraoperative image T1 is obtained, and the simulation information S0 is registered with the intraoperative image T0 based on the positional information P0 to display the simulation information S0 superimposed on the intraoperative image T0. Since the positional information P0 is obtained based on the unchanged position included in the intraoperative image T0, information necessary to achieve the registration is obtained not from the entire intraoperative image T0. This allows obtaining the positional information P0 with a smaller amount of computation, thereby allowing quick registration of the simulation information S0 with the intraoperative image T0 to display the superimposed image.

While specification of the unchanged position is received and template matching is performed based on the unchanged position to obtain the positional information P0 in the above-described embodiment, the unchanged position may be automatically detected. For example, the liver, which is the part being operated on, may be extracted from the initial intraoperative image T1, and feature points such as the edges of a part contained in a region other than the extracted liver may be detected as the unchanged position. In this case, the positional information P0 may be obtained by performing template matching using the detected feature points.

In this case, the feature points may be detected every time the positional information P0 is obtained. However, the tablet-type terminal is not rapidly moved during imaging, and it is preferred that the positional information P0 be obtained using feature points that are used to calculate the previous positional information P0. This allows reducing the amount of computation to quickly calculate the information for the registration.

With respect to the above-described embodiment, there may be cases where the intraoperative image T0 is momentarily whites out due to influence of the illumination of the operating room. At that time, the positional information P0 cannot be obtained from the white-out frame of the intraoperative image T0. The tablet-type terminal is not rapidly moved during imaging, and, if the positional information P0 cannot be obtained from the intraoperative image T0, the simulation information S0 may be registered with the intraoperative image T0 using the positional information P0 that is calculated using the previous frame of the intraoperative image T0. This allows preventing a situation where no simulation information S0 is displayed on the display 15 even momentarily.

Figure 9:
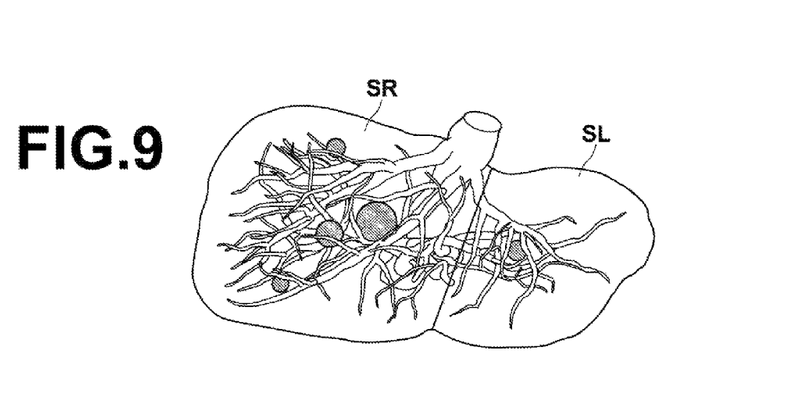
FIG. 9 is a diagram showing two pieces of simulation information.

Further, while one piece of simulation information S0 is generated in the above-described embodiment, pieces of simulation information S0 may be generated. For example, there may be a case where the part being operated on is the liver, and the left lobe of the liver is excised. To address such a case, the simulation information obtaining unit 22 may obtain two pieces of simulation information including right lobe simulation information SR and left lobe simulation information SL, as shown in FIG. 9. In this case, the initial registration is performed for each of the right lobe simulation information SR and the left lobe simulation information SL to register each simulation information with the intraoperative image T0. Specifically, the initial registration is performed such that the right lobe simulation information SR is registered with the right lobe in the intraoperative image T0 and the left lobe simulation information SL is registered with the left lobe in the intraoperative image T0.

When the left lobe of the liver is excised during a surgery, the position of the left lobe is changed from the position before the surgery. In this case, with respect to the simulation information SL for the left lobe to be excised, specification of a changeable position which is moved during the surgery, such as edges of the left lobe, is received in place of specification of an unchanged position. Then, the left lobe simulation information SL is registered with the intraoperative image T0 based on the specified changeable position.

In this case, the positional information obtaining unit 24 obtains the positional information PR and PL for the right lobe simulation information SR and the left lobe simulation information SL, respectively. The positional information PR for the right lobe is obtained based on an unchanged position, similarly to the above-described embodiment. The positional information PL for the left lobe is obtained based on the changeable position. It should be noted that the positional information PL for the left lobe corresponds to additional positional information of the invention.

Figure 10:
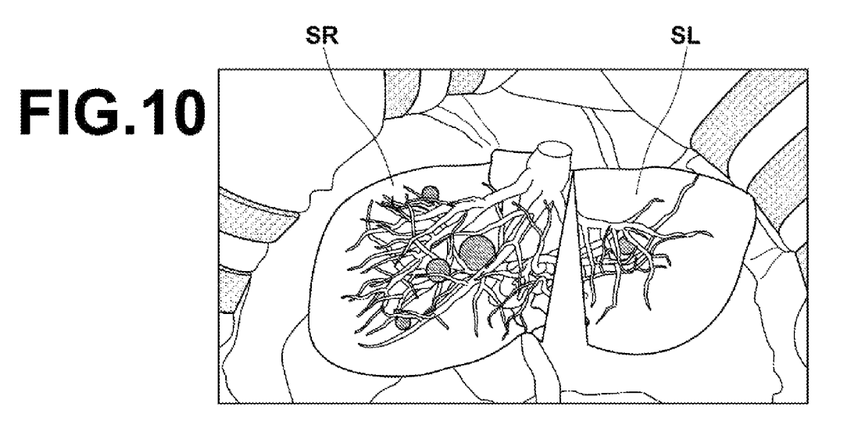
FIG. 10 is a diagram showing a state where the pieces of simulation information superimposed on the right lobe and the left lobe of the liver after excision, respectively, are displayed.

Then, based on the positional information PR and PL, the superimpose display unit 25 registers the simulation information SR and SL with the intraoperative image T0. In this case, the simulation information SR for the right lobe is registered using the positional information PR which is obtained based on the unchanged position, and is superimposed and displayed on the position of the right lobe in the simulation information SR, similarly to the above-described embodiment. On the other hand, the simulation information SL for the left lobe is registered using the positional information PL which is obtained based on the changeable position, and, when the position of the left lobe is changed by excision, the simulation information SL is superimposed on the intraoperative image T0 to follow the change of the position. In this manner, the simulation information SR and SL are superimposed and displayed on the excised right lobe of the liver and the left lobe of the liver, respectively, as shown in FIG. 10.

Further, while the simulation information S0 superimposed on the intraoperative image T0 is displayed on the tablet-type terminal in the above-described embodiment, the present invention is also applicable to registration of the simulation information S0 with the intraoperative image in a case where the intraoperative image is displayed on a head mount display. The present invention is also applicable to a case where the intraoperative image T0 is taken with a camera placed above the operating table, and the simulation information S0 is registered with the image taken with the camera and displayed on a display device in the operating room or outside the operating room. In this case, the image registration device 1 according to this embodiment is installed on a computer, and the registration between the intraoperative image T0 and the simulation information S0 is performed on the computer. Then, the simulation information S0 superimposed on the intraoperative image T0 is displayed on the head mount display and the display device connected to the computer.

Further, while the projection image of the liver extracted from the three-dimensional image V0 is used as the simulation information S0 in the above-described embodiment, this is not intended to limit the invention. As the simulation information, a functional three-dimensional image obtained through a PET test or a NM test (nuclear medicine test) may be used. Further, the simulation information S0 is not limited to image information, and lines indicating a position of excision, symbols such as arrows, textual information such as names of parts and tissues around the position of excision, or the like, may be used as the simulation information. The image information, symbols, and textual information may be used in combination as the simulation information.

Further, while the simulation information obtaining unit 22 generates the simulation information S0 in the above-described embodiment, the simulation information S0 may be generated by a simulation information obtaining unit which is provided separately from the image registration device 1. In this case, the image registration device does not need to include the simulation information obtaining unit 22, and the configuration of the image registration device can be simplified.

Further, while the initial registration is achieved by moving and deforming the simulation information S0 in the above-described embodiment, the initial registration may be achieved by preparing pieces of simulation information oriented in various directions in advance and selecting the simulation information that is most suited to the orientation of the part being operated on included in the intraoperative image T0 at the initial registration.

Further, while the hepatic artery, etc., included in the liver are extracted and included in the simulation information S0 in the above-described embodiment, only the liver, which is the part being operated on, mat be extracted, and an image that represents the three-dimensional shape of only the liver may be used as the simulation information S0. In this case, the simulation information S0 may include only the contour of the liver.

Further, while the liver is used as the part being operated on in the above-described embodiment, this is not intended to limit the invention. The invention is applicable to cases where the part being operated on is any body part and the simulation information S0 superimposed on the intraoperative image T0 is displayed.

What is claimed is:
1. An image registration device comprising:
   at least one hardware processor configured to implement:
      sequentially obtaining an intraoperative image including a part being operated on in a human body during a surgery;
      obtaining simulation information relating to the surgery of the part being operated on;

performing initial registration between the intraoperative image and the simulation information;

obtaining positional information indicating a relative positional difference between the intraoperative image after the initial registration and a newly obtained intraoperative image based on an unchanged position included in a portion of the part which will remain after the excision of the part in a case where the portion of the part being operated on is excised; and a superimpose display unit for registering the simulation information with the new intraoperative image based on the positional information, and displaying on a display the simulation information superimposed on the new intraoperative image, wherein the at least one hardware processor configured to implement:

obtaining additional simulation information relating to a portion of the part being operated on, the portion being moved during the surgery, performing initial registration between the intraoperative image and the additional simulation information, obtaining, for the additional simulation information, additional positional information indicating a relative positional difference between the intraoperative image after the initial registration and the newly obtained intraoperative image based on a changeable position included in the portion that is moved during the surgery, and wherein the superimpose display unit registers the additional simulation information with the new intraoperative image based on the additional positional information and further displays, on the display, the additional simulation information superimposed on the new intraoperative image.

2. The image registration device as claimed in claim 1, wherein the at least one hardware processor is configured to implement receiving specification of the unchanged position.

3. The image registration device as claimed in claim 1, wherein the at least one hardware processor is configured to implement obtaining a three-dimensional image about the part being operated on, and generating the simulation information based on the three-dimensional image.

4. The image registration device as claimed in claim 1, wherein, in a case where the part being operated on includes at least one structure, the simulation information comprises an image representing three-dimensional shapes of the part being operated on and the at least one structure.

5. The image registration device as claimed in claim 4, wherein the image representing the three-dimensional shapes includes only contours of the part being operated on and the at least one structure.

6. The image registration device as claimed in claim 4, wherein the image representing the three-dimensional shapes has different transparency levels set for the part being operated on and the at least one structure.

7. The image registration device as claimed in claim 4, wherein the image representing the three-dimensional shapes has different colors set for the part being operated on and the at least one structure.

8. The image registration device as claimed in claim 1, wherein the simulation information comprises an image representing a three-dimensional shape of the part being operated on.

9. The image registration device as claimed in claim 8, wherein the image representing the three-dimensional shape includes only a contour of the part being operated on.

10. The image registration device as claimed in claim 1, wherein the simulation information comprises a functional three-dimensional image of the part being operated on.

11. The image registration device as claimed in claim 1, wherein the at least one hardware processor is configured to implement obtaining, as the positional information, at least one of a translational component, a rotational component, and an enlargement factor between the intraoperative image after the initial registration and the newly obtained intraoperative image.

12. An image registration method comprising the steps of:

sequentially obtaining an intraoperative image including a part being operated on in a human body during a surgery;

obtaining simulation information relating to the surgery of the part being operated on;

performing initial registration between the intraoperative image and the simulation information;

obtaining positional information indicating a relative positional difference between the intraoperative image after the initial registration and a newly obtained intraoperative image based on an unchanged position included in a portion of the part which will remain after the excision of the part in a case where the portion of the part being operated on is excised;

registering the simulation information with the new intraoperative image based on the positional information, and displaying, on a display unit, the simulation information superimposed on the new intraoperative image;

obtaining additional simulation information relating to a portion of the part being operated on, the portion being moved during the surgery;

performing initial registration between the intraoperative image and the additional simulation information;

obtaining, for the additional simulation information, additional positional information indicating a relative positional difference between the intraoperative image after the initial registration and the newly obtained intraoperative image based on a chargeable position included in the portion that is moved during the surgery; and registering the additional simulation information with the new intraoperative image based on the additional positional information and further displaying, on the display unit, the additional simulation information superimposed on the new intraoperative image.

13. A non-transient recording medium containing an image registration program for causing a computer to execute the steps of:

sequentially obtaining an intraoperative image including a part being operated on in a human body during a surgery;

obtaining simulation information relating to the surgery of the part being operated on;

performing initial registration between the intraoperative image and the simulation information;

obtaining positional information indicating a relative positional difference between the intraoperative image after the initial registration and a newly obtained intraoperative image based on an unchanged position included in a portion of the part which will remain after the excision of the part in a case where the portion of the part being operated on is excised;

registering the simulation information with the new intraoperative image based on the positional information, and displaying, on a display unit, the simulation information superimposed on the new intraoperative image;

obtaining additional simulation information relating to a portion of the part being operated on, the portion being moved during the surgery;

performing initial registration between the intraoperative image and the additional simulation information;

obtaining, for the additional simulation information, additional positional information indicating a relative positional difference between the intraoperative image after the initial registration and the newly obtained intraoperative image based on a changeable position included in the portion that is moved during the surgery; and registering the additional simulation information with the new intraoperative image based on the additional positional information and further displaying, on the display unit, the additional simulation information superimposed on the new intraoperative image.

* * * * *